US00PP09756P

United States Patent [19]

Harring

[11] Patent Number: Plant 9,756

[45] Date of Patent: Dec. 17, 1996

[54] GERANIUM PLANT NAMED 'HWD ONYX'

[75] Inventor: Gabriele Harring, Kerpen, Germany

[73] Assignee: Dummen Jungpflanzenkulturen, Rheinberg-Eversael, Germany

[21] Appl. No.: 520,862

[22] Filed: Aug. 30, 1995

[51] Int. Cl.[6] ..... A01H 5/00

[52] U.S. Cl. ..... Plt./87.12

[58] Field of Search ..... Plt./87.12

*Primary Examiner*—James R. Feyrer

*Attorney, Agent, or Firm*—Proprietary Rights International

[57] ABSTRACT

A new and distinct cultivar of geranium plant named HWD Onyx, characterized by its light pink petals with purple lines at base; early flowering; freely branching; and compact plant habit.

1 Drawing Sheet

The present invention relates to a new and distinct cultivar of geranium plant, botanically known as *Pelargonium*× *peltatum,* known as the variety Dueony, and hereinafer referred to by the cultivar name HWD Onyx.

The new cultivar is a product of a planned breeding program conducted by the inventor in Rheinberg, Germany. The objective of the breeding program was to develop a new ivy geranium with white flowers and compact plant habit.

The new cultivar originated from a cross made by the inventor of the proprietary selection P79-3-3 as the male or pollen parent with the proprietary selection P80-4-7 as the female or seed parent.

The cultivar HWD Onyx was discovered and selected by the inventor as a flowering plant within the progeny of the stated cross in a controlled environment in Rheinberg, Germany. Asexual reproduction of the new cultivar by terminal cuttings taken at Rheinberg, Germany, has shown that the unique features of this new geranium are stabilized and reproduced true to type in successive generations of asexual reproduction.

The following traits have been repeatedly observed and are determined to be the unique characeristics of HWD Onyx. These characteristics in combination distinguish HWD Onyx as a new and distinct cultivar:

1. Light pink petals with purple lines at base.
2. Early flowering.
3. Freely branching.
4. Compact plant habit.

In comparison to the parent selection P79-3-3, plants of the new geranium have larger flowers. In comparison to the parent selection P80-4-7, plants of the new geranium flower earlier and have smaller flowers.

The new geranium is similar in flower color to the nonpatented cultivar Schneekönigin. Compared to plants of the cultivar Schneekönigin, plants of the new Geranium are more compact in plant habit, flower earlier and have shorter internodes.

The accompanying colored photograph illustrates the overall appearance of the new cultivar, showing the colors as true as it is reasonably possible to obtain in colored reproductions of this type. The petal color in the photograph appears lighter than the actual petal color due to light reflectance. The photograph comprises a top perspective view of a typical potted plant of HWD Onyx with one plant in a 10-cm container.

The cultivar HWD Onyx has not been observed under all possible environmental conditions. The phenotpe may vary somewhat with variations in environment such as temperature and light intensity, without, however, any variance in genotype. The following observations, measurements and comparisons describe plants grown in Rheinberg, Germany, under commercial practice in a glass-covered greenhouse with day temperatures of 24° C. and night temperatures of 18° to 20° C. and light levels of 45,000 to 60,000 lux. Plants were grown in 10-cm pots with one plant per pot.

In the following description, color references are made to The Royal Horticultural Society Colour Chart except where general terms of ordinary dictionary significance are used.

Classification:

*Botanical.*—*Pelargonium*×*peltatum.*

*Commercial.*—Ivy Geranium.

*Cultivar.*—'HWD Onyx'.

Parentage:

*Male parent.*—Proprietary selection P79-3-3.

*Female parent.*—Proprietary selection P80-4-7.

Propagation:

*Type cutting.*—Terminal cuttings.

*Time to initiate roots.*—Summer: 27° C., 21 days; winter: 20° C., 28 days.

Plant Description

General appearance: Spreading; pendant; freely branching.

Foliage description:

*Arrangement.*—Generally alternate.

*Shape.*—Orbicular with acute tip and cordate base.

*Size.*—Length: 5 to 6 cm. Width: 5 to 7 cm.

*Texture.*—Leathery; pubescent on upper and under surfaces.

*Margin.*—Palmately lobed.

*Color.*—Young foliage, upper surface: 137A. Young foliage, under surface: 137C. Mature foliage, upper surface: 137A. Mature foliage, under surface: 137C. Zonation pattern: None. Veins, upper surface: 146C. Veins, under surface: 146C. Petiole: 146B.

*Venation pattern.*—Palmate.

*Petiole.*—Length: 3 to 4 cm. Diameter: 2 to 3 mm.

Stem description:

*Internode length.*—1.8 to 2.5 cm.

*Stem color.*—146B.

*Lateral branch number.*—22.

*Lateral branch length.*—7.5 to 14.5 cm.

Flowering Description

Flowering habit: Freely flowering. Flowers arranged in umbels.

Natural flowering season: Year-round.

Flowers borne: Flower buds develop in apical leaf axils. Umbels are displayed above the foliage.

Quantity of inflorescences: Very floriferous; usually 28 umbels per plant at various stages of development.

Umbels:

*Form.*—Rectangular.

*Diameter.*—8 to 11 cm.

*Depth (height).*—5 to 6 cm.

Flowers:

*Form.*—Semi-double.

*Shape.*—Rounded.

*Quantity of flowers per umbel.*—6 to 8.

*Diameter.*—4.5 to 5.5 cm.

*Depth (height).*—2 cm.

Petals:

*Shape.*—Rounded.

*Arrangement.*—Rosette, overlapping.

*Quantity.*—7 to 9 .

*Aspect.*—Flat.

*Size.*—Length: 2 to 3 cm. Width: 1.5 to 2 cm.

*Texture.*—Satiny, smooth.

*Margin.*—Entire, wavy.

*Color.*—When opening, upper surface: 155D with lines of 61A on two or three petals. When opening, under surface: 155D. Upper surface: 69D at margin fading to 69C in center with lines of 70C at base of two or three petals. Under surface: 69D at margin fading to 155D to base. Fading to: Fading not observed.

Petaloids:

*Shape.*—Irregular, generally obovate.

*Arrangement.*—Rosette, overlapping.

*Quantity.*—3 to 5.

*Size.*—Length: 1.5 to 2 cm. Width: 1 to 1.5 cm.

*Texture.*—Satiny, smooth.

*Margin.*—Slightly wavy.

*Color.*—When opening, upper surface: 155C with lines of 61A at base of petal. When opening, under surface: 155C. Upper surface: 69D with spots of 61A. Under surface: 69D. Fading to: Fading not observed.

Peduncle (umbel stem):

*Angle.*—Erect, rigid.

*Length.*—9 to 11 cm.

*Pubescence.*—Very fine.

*Color.*—146B.

Pedicel (individual flower stem):

*Angle.*—Erect, rigid.

*Length.*—3 to 3.5 cm.

Pubescence.—Very fine.

*Color.*—146B at base, 71A at apex.

Flower bud:

*Shape.*—Ovoid.

*Length.*—1 to 2 cm.

*Diameter.*—0.5 to 1 cm.

*Color.*—Combination of 158D and 155D with streaks of 186B at base.

Sepals:

*Arrangement.*—Rosette.

*Quantity.*—5 to 6.

*Size.*—Length: 1 to 1.25 cm. Width: 2 to 4 cm.

*Shape.*—Acuminate with apiculate tip.

*Texture.*—Velvety.

*Margin.*—Entire.

*Color.*—Upper surface: 144A. Under surface: 144A.

Reproductive organs:

*Androecium.*—Stamen number: 14 to 18. Anther size: 2 to 3 mm. Anther color: 187A. Pollen color: 173B.

*Gynoecium.*—Pistil number: 1. Pistil length: 1 cm. Stigma shape: Decurrent. Stigma color: 182C. Style length: 2 mm. Style color: 159A.

Ploidy level: Tetrapolod.

Disease resistance: No fungal, bacterial nor viral problems observed.

Seed development: Seed production is very rarely observed.

It is claimed:

1. A new and distinct cultivar of geranium plant named HWD Onyx, as illustrated and described.

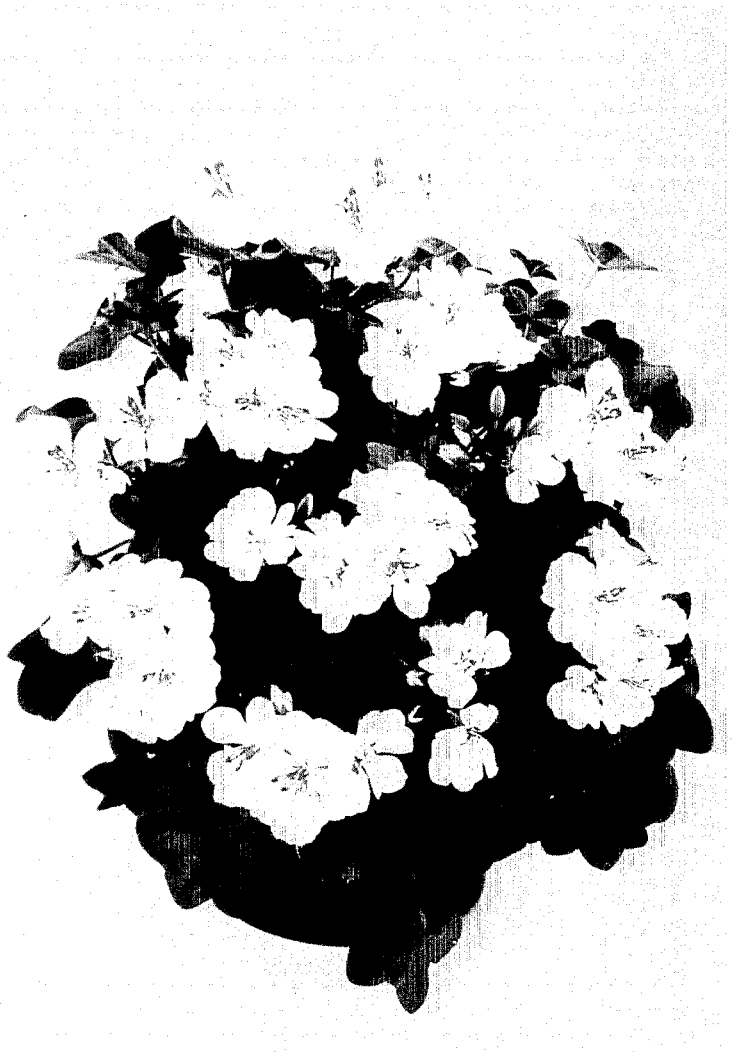

* * * * *